March 17, 1959 F. MEILLAND Plant Pat. 1,821
ROSE PLANT
Filed July 25, 1958 2 Sheets-Sheet 1
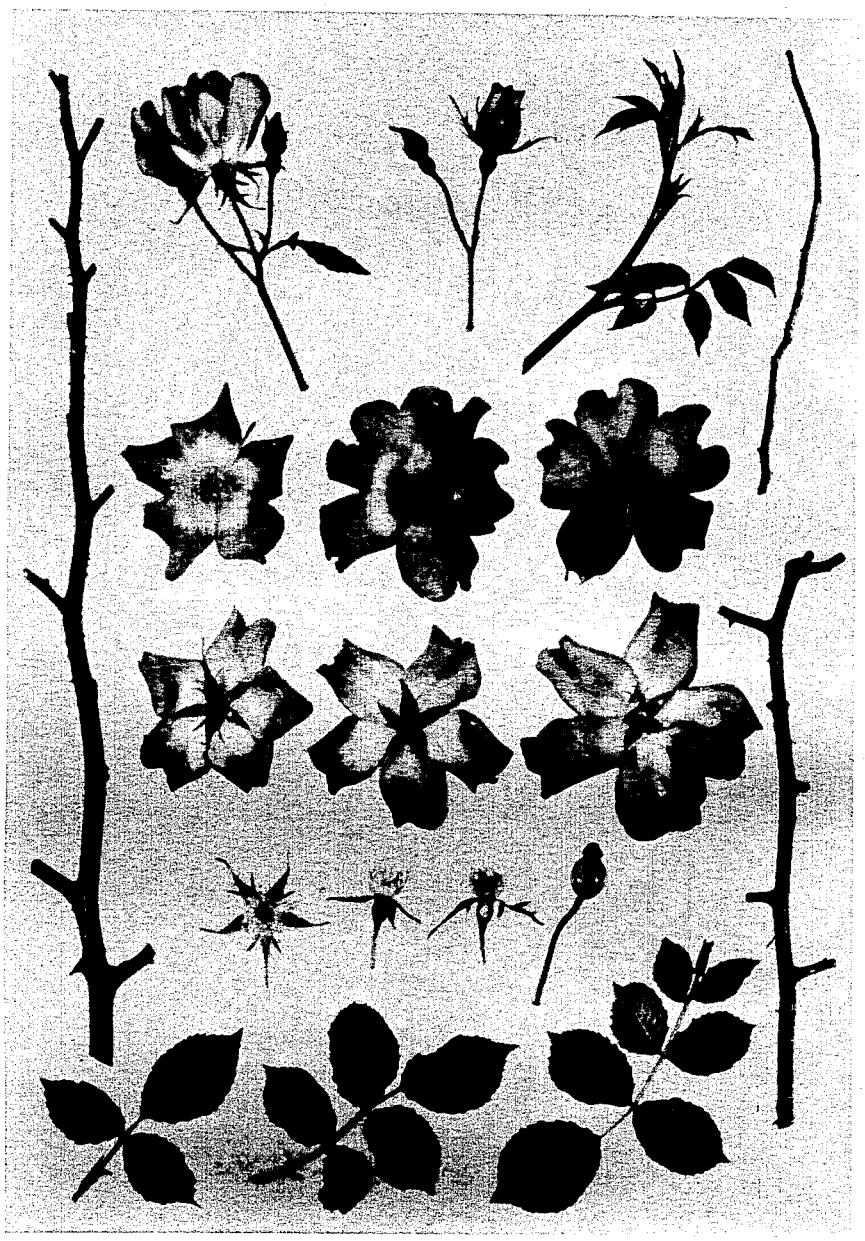
Francis Meilland, Deceased
By: Marie Louise Meilland née Paolino,
Legal Representative
INVENTOR
BY Robb & Robb
ATTORNEYS March 17, 1959 F. MEILLAND Plant Pat. 1,821
ROSE PLANT
Filed July 25, 1958 2 Sheets-Sheet 2
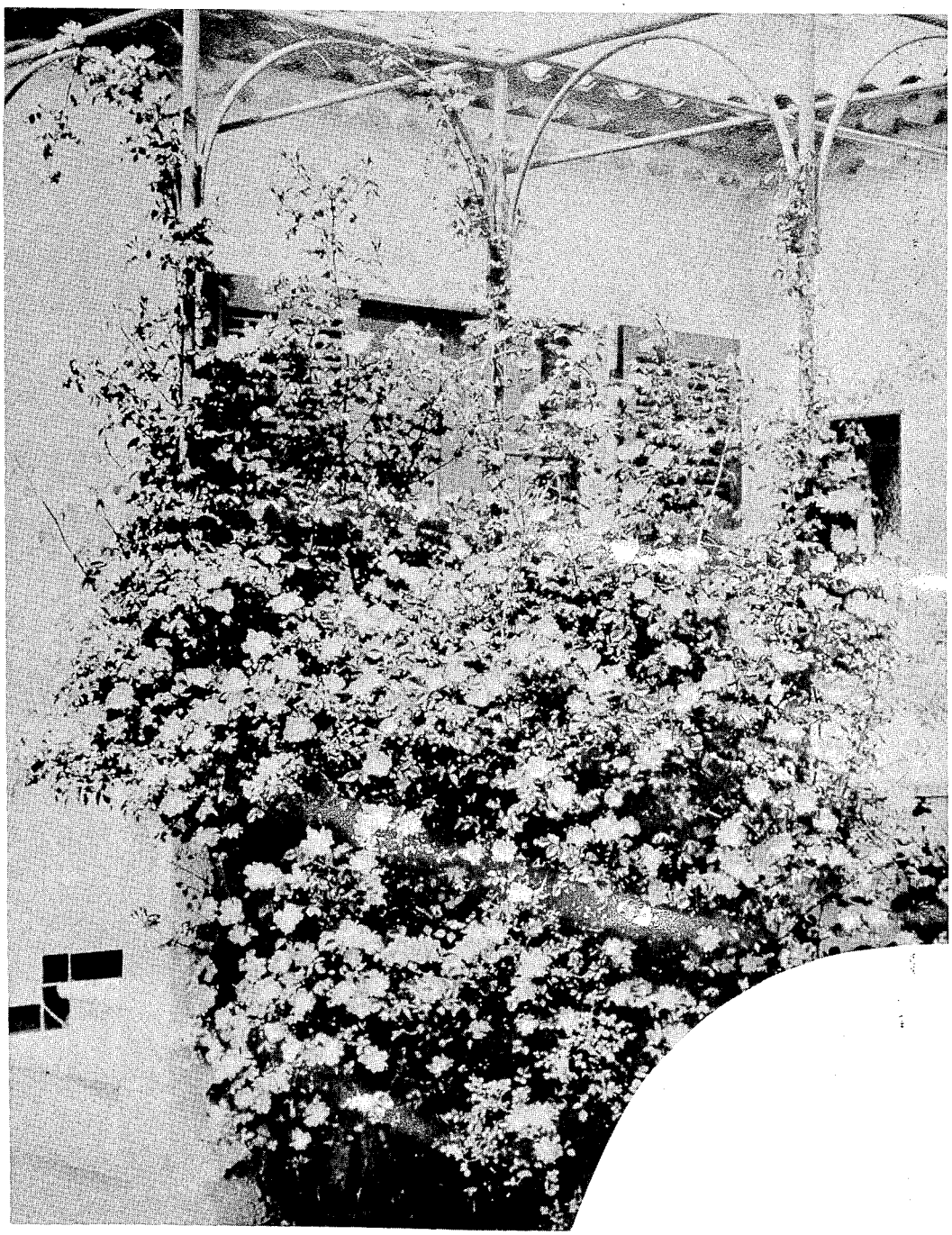
INVENTOR
Francis Meilland, Deceased
By: Marie Louise Meilland née Paolino,
Legal Representative
BY Robb & Robb
ATTORNEYS United States Patent Office Plant Pat. 1,821
Patented Mar. 17, 1959

1,821

ROSE PLANT

Francis Meilland, deceased, late of Cap D'Antibes, France, by Marie Louise Meilland, née Paolino, legal representative, Cap D'Antibes, France, assignor to The Conard-Pyle Company, West Grove, Pa., a corporation of Pennsylvania Application July 25, 1958, Serial No. 751,102

Claims priority, application France July 29, 1957

1 Claim. (Cl. 47—61)

The present invention relates to a new and distinct variety of rose plant of the climbing polyantha class, which was originated by the deceased by crossing an unnamed and unpatented seedling derived from a cross of the variety "Independence" (U. S. Plant Patent No. 1,036), known in Europe as "Kordes' Sondermeldung"×"Orange Triumph" (unpatented) with the variety "Phyllis Bide" (unpatented).

The primary objective of this breeding was to produce a new variety of climbing or pillar rose possessing the same brilliant coloration of the parent variety "Phyllis Bide," but having a more continuous or remontant blooming habit, together with more prolific blooms than are normally produced by the well-known variety "Phyllis Bide." This objective was fully achieved, along with other improvements, as evidenced by the following characteristics which are outstanding in the new variety and represent a unique combination which definitely differentiates it from its parents as well as all other varieties of which the deceased was aware:

(1) Good, attractive and glossy green foliage;

(2) Single type blooms of medium size;

(3) A distinctive Geranium Red coloration of the upper half of the flower petals, with Primrose Yellow color in the lower half, giving the appearance of aureole in the center of the bloom;

(4) An almost continuous recurrence of bloom throughout the growing season; and (5) A distinctive and remarkable mass effect of the blooms at each bloom peak.

Asexual reproduction of the new variety, by budding, as performed in France and also at West Grove, Pennsylvania, U. S. A., shows that the foregoing characteristics and distinctions come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character, and also a complete climbing plant depicting in black-and-white its climbing habit and the mass effect of the blooms.

The following is a detailed description of the new variety, with color terminology in accordance with the Oberthur color chart, except where general color terms of ordinary dictionary significance are obvious:

Type: Hardy; climbing; outdoor; seedling; for garden decoration.

Class: Climbing polyantha.

Breeding: Seedling.

*Seed parent.*—An unnamed seedling derived from a cross of "Independence"×"Orange Triumph."

*Pollen parent.*—"Phyllis Bide."

Propagation: Holds its distinguishing characteristics through succeeding propagations by budding.

*Flower*

Locality where grown and observed: West Grove, Pennsylvania, U. S. A.

Flowers borne: Several to stem; in regular clusters; on stems of medium length and normal strength.

Quantity of bloom: Abundant, outdoors.

Continuity: Continuous.

Fragrance: Slight. Nature—spicy.

Bud:

*Peduncle.*—Medium length; medium caliper; erect; rough; with numerous red prickles. Color—reddish.

*Before calyx breaks.* — Size — medium. Form — pointed; with a conspicuous neck; with foliaceous appendages on the surface of the bud; with slender, bristle-like foliaceous parts extending beyond the tip of the bud equal to ¼ or more of its length.

*As calyx breaks.* — Color — Cochineal Carmine, Plate 116, tone 4, streaked with yellow.

*As first petal opens.*—Size—medium. Form—medium length; pointed ovoid. Color: Outside—Cochineal Carmine, Plate 116, tone 4; inside—Geranium Red, Plate 111, tone 4.

*Opening.*—Opens up well.

Bloom:

*Size (when fully open).*—Medium; from 2½ to 2¾ inches.

*Petalage.*—Single; 5 petals; arranged regularly.

*Form.*—Open at first, but becoming flat-open; petals at first being loosely rolled inward, but later becoming flat at maturity.

Petals: Medium thickness; with inside satiny and outside shiny. Shape—obovate; generally with 2 notches.

This description of a newly opened flower was made from a rose grown outdoors in the month of June at West Grove, Pennsylvania, U. S. A.:

*Color.*—Outside surface—Geranium Red, Plate 111, tone 4 over the upper ⅓ of the petal, becoming speckled with Primrose Yellow, Plate 19, tone 2 extending unadultered over the lower ⅔ of the petal. Inside surface—Geranium Red, Plate 111, tone 4 covering the upper half of the petal, becoming speckled with Primrose Yellow, Plate 19, tone 3 at the middle of the petal and merging into a clear Primrose Yellow, Plate 19, tone 3 over the lower half of the petal.

This description was made from a rose that was open for 3 days outdoors in the month of June, at West Grove, Pennsylvania, U. S. A.:

*Color.*—Outside surface—Crimson Carmine, Plate 159, tone 2 over upper ⅓ of the petal, becoming suffused with Violet Rose, Plate 154, tone 3, and then with Amber White, Plate 12, tone 1, with the latter color extending to the base of the petal. Inside surface—Fuchsin Red, Plate 160, tone 4 over the upper ⅔ of the petal, grading to Crimson Carmine, Plate 159, tone 2, and to Amber White, Plate 12, tone 1 at the base of the petal.

*General color effect.*—Newly opened flower—Geranium Red, Plate 111, tone 4 over upper half of the petal, becoming Primrose Yellow, Plate 19, tone 3 over the lower half of the petal. 3-days open—Fuchsin Red, Plate 160, tone 4 over the upper ⅔ of the petal, grading to Crimson Carmine, Plate 159, tone 2.

*Behavior.*—Drop off cleanly.

*Flower longevity.*—On bush in garden—4 days in June. Cut roses grown outdoors and kept at living-room temperatures—3 days in June.

*Reproductive organs*

Stamens: Medium number; arranged regularly about pistils.

Filaments: Most with anthers; medium length. Color—Begonia Rose, Plate 123, tone 2, with base Primrose Yellow, Plate 19, tone 4.

Anthers: All open at once; no anther fused with a petaloid or a pistil. Color—reddish brown.

Pollen: Moderate abundance. Color—yellow.

Pistils: Medium number.

Styles: Even; from short to medium length; medium heavy; bunched.

Stigma: Color—pale yellow.

Ovaries: All enclosed in receptacle.

Hips: None observed.

Sepals: Permanent; medium length; straight.

Seeds: None observed.

*Plant*

Foliage:

*Leaves.*—Compound of 7 leaflets; abundant; medium size; leathery; glossy.

*Leaflets.*—Shape — oval, with apex acuminate. Base—obtuse. Margin—irregularly serrate.

*Color.*—Mature: Upper surface—Quaker Green, Plate 271, tone 3; under surface—Quaker Green, Plate 271, tone 1. Young: upper surface—Moss Green, Plate 272, tone 1, overlaid with Antique Red, Plate 104, tone 4; under surface—Moss Green, Plate 272, tone 1, overlaid with Antique Red, Plate 104, tone 4.

*Rachis (the supporting stem of the compound leaf).*—From light to medium. Upper side—grooved; hairy. Under side—sparsely prickly.

*Stipules.*—Moderately long; medium width; with points of medium length turning out at an angle of more than 45°.

*Disease resistance.*—Comparable to that of the average variety grown under the same cultural conditions at West Grove, Pennsylvania, U. S. A.

Growth:

*Habit.*—Climbing; much-branched.

*Growth.*—Free; vigorous.

*Canes.*—Medium caliper.

*Main stems.*—Bright. Color—Quaker Green, Plate 271, tone 2, sometimes with a reddish overcast on the side facing the sun. Prickles—several; color — Mineral Brown, Plate 338, tone 4. Hairs—none.

*Branches.*—Bright. Color—Quaker Green, Plate 271, tone 2, sometimes with a reddish overcast on the side facing the sun. Prickles—several; color—Purple Brown, Plate 166, tone 4. Hairs—none.

*New shoots.*—Dull. Color—Vinous Purple, Plate 171, tone 4, overlying Moss Green, Plate 272, tone 2. Prickles—several; color—Plum Violet, Plate 172, tone 4. Hairs—few; color—Vinous Purple, Plate 171, tone 4.

What is claimed is:

A new and distinct variety of rose plant of the climbing polyantha class, substantially as herein shown and described, characterized particularly as to novelty by the unique combination of good, attractive and glossy green foliage, single-type blooms of medium size, a distinctive Geranium Red and Primrose Yellow coloration of the upper and lower halves, respectively, of the flower petals, giving the appearance of aureole in the center of the bloom, an almost continuous recurrence of the bloom throughout the growing season, and a distinctive and remarkable mass effect of the blooms at each bloom peak.

No references cited.